United States Patent
Burnside et al.

(10) Patent No.: US 6,287,599 B1
(45) Date of Patent: Sep. 11, 2001

(54) SUSTAINED RELEASE PHARMACEUTICAL DOSAGE FORMS WITH MINIMIZED PH DEPENDENT DISSOLUTION PROFILES

(75) Inventors: Beth A. Burnside, Brookeville; Rong-Kun Chang, Rockville; Xiaodi Guo, Derwood, all of MD (US)

(73) Assignee: Shire Laboratories, Inc., Rockville, MD (US)

( * ) Notice: Subject to any disclaimer, the term of this patent is extended or adjusted under 35 U.S.C. 154(b) by 0 days.

(21) Appl. No.: 09/741,548

(22) Filed: Dec. 20, 2000

(51) Int. Cl.[7] .................................................. A61K 9/22
(52) U.S. Cl. ................................................ 424/468
(58) Field of Search ............................... 424/468

(56) References Cited

U.S. PATENT DOCUMENTS

| 4,968,508 | * | 11/1990 | Oren et al. | 424/468 |
| 5,102,668 | * | 4/1992 | Eichel et al. | 424/490 |
| 5,378,474 | * | 1/1995 | Morella et al. | 424/469 |

* cited by examiner

*Primary Examiner*—Raymond Henley, III
(74) *Attorney, Agent, or Firm*—Elliot M. Olstein; Raymond J. Lillie

(57) ABSTRACT

A pharmaceutical composition comprising at least one pharmaceutically active agent that is pH dependent, at least one non-pH dependent sustained release agent, and at least one pH dependent agent that increases the dissolution rate of the at least one pharmaceutically active agent at a pH in excess of 5.5. Such compositions have minimized pH-dependent dissolution profiles or pH-independent dissolution profiles.

30 Claims, 1 Drawing Sheet

Figure 1:
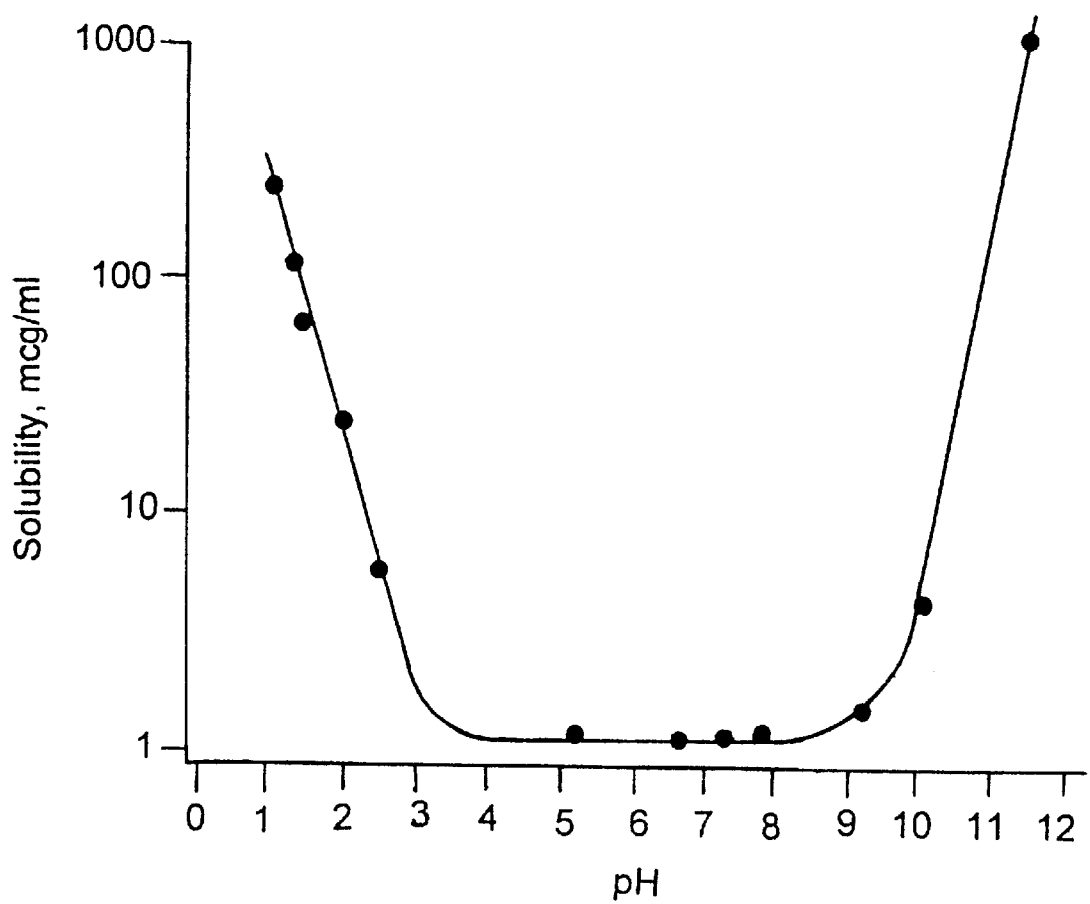

SUSTAINED RELEASE PHARMACEUTICAL DOSAGE FORMS WITH MINIMIZED PH DEPENDENT DISSOLUTION PROFILES

This invention relates to pharmaceutical compositions. More particularly, this invention relates to pharmaceutical compositions having a pH-independent or a minimized pH-dependent dissolution profile. In particular, such composition includes at least one pharmaceutically active agent that has a pH dependent solubility profile, at least one non-pH-dependent sustained release agent, and at least one pH-dependent agent that increases the dissolution rate of the at least one pharmaceutically active agent at a pH in excess of 5.5. The active agent(s) has (have) a solubility profile wherein the active agent(s) is (are) more soluble in an acidic medium than in a basic medium.

The rate at which a drug goes into solution when it is dissolved in a medium is proportional to the solubility of the drug in the medium. Many drugs have different solubilities at different pHs. These pH-dependent solubility differences lead to pH-dependent dissolution profiles. In general, pH-dependent dissolution is an undesirable product characteristic.

Compressed matrix tablets containing a basic drug often give a faster dissolution profile in simulated gastric fluid, having a pH about 1.0, than in simulated intestinal fluid (pH 6.8 to 7.4).

It is an object of the present invention to provide a pharmaceutical composition with a minimized pH dependent or a pH-independent dissolution profile.

In accordance with an aspect of the present invention, there is provided a pharmaceutical composition. The composition comprises at least one pharmaceutically active agent that is pH dependent, at least one non-pH dependent sustained release agent, and at least one pH-dependent agent that increases the rate of release of the at least one pharmaceutically active agent from the tablet at a pH in excess of 5.5, such as at least one organic acid that maintains an acidic micro-environment in the tablet.

Pharmaceutically active agents which are pH dependent and which may be included in the composition include, but are not limited to, weakly basic drugs and their salts that have higher solubilities at lower pH levels. Such drugs include, but are not limited to, guanfacine hydrochloride, guanadrel sulfate, reserpine, anagrelide hydrochloride, propanolol, metoprolol, atenolol, timolol, erthyrthromycin, clonidine, chlorpheniramine, bromopheniramine, diltiazen, and scopolamine. In general, the pharmaceutically active agent is present in the composition in an amount of from about 0.1 wt, % to about 70 wt. %, preferably from about 1 wt. % to about 40 wt %. In one embodiment, the at least one pharmaceutically active agent is guanfacine hydrochloride. In another embodiment, the at least one pharmaceutically active agent is anagrelide hydrocholoride. It is to be understood, however, that the scope of the present invention is not to be limited to any particular pharmaceutically active agent.

Non-pH-dependent sustained release agents which may be included in the composition include, but are not limited to, ethylcellulose, cellulose acetate, vinyl acetate/vinyl chloride copolymers, acrylate/methacrylate copolymers, polyethylene oxide, hydroxypropyl methylcellulose, carrageenan, alginic acid and salts thereof, hydroxyethyl cellulose, hydroxypropyl cellulose, karaya gum, acacia gum, tragacanth gum, locust bean gum, guar gum, sodium carboxymethyl cellulose, methyl cellulose, beeswax, carnauba wax, cetyl alcohol, hydrogenated vegetable oils, and stearyl alcohol. In general, the at least one non-pH-dependent sustained release agent is present in the composition in an amount of from about 5 wt. % to about 50 wt. %, preferably from about 10 wt. % to about 30 wt. %. It is to be understood, however, that the scope of the present invention is not to be limited to any particular non-pH-dependent sustained release agents.

pH-dependent agents that increase the rate of release of the at least one pharmaceutically active agent from the tablet at a pH in excess of 5.5 include, but are not limited to, polymers that swell at a pH in excess of 5.5, and enteric agents, and/or agents that increase the solubility of the at least one pharmaceutically active agent at a pH greater than 5.5, by maintaining an acidic microenvironment in the tablet, e.g., an organic acid. The at least one pH-dependent agent is present in the composition in an amount of from about 0.5 wt. % to about 40 wt. %, preferably from about 1 wt. % to about 20 wt. %.

Polymers that swell at a pH in excess of 5.5 include, but are not limited to, acrylic acid copolymers, sodium alginate, carrageenan, alginic acid, pectin, and sodium carboxymethyl cellulose.

Enteric agents include, but are not limited to, cellulose acetate phthalate, hydroxypropyl methylcellulose phthalate, polyvinyl acetate phthalate, methacrylic acid coplymers, cellulose acetate trimellitate, hydroxypropyl methylcellulose acetate, succinate, shellac, and zein.

Agents that increase the solubility of the at least one pharmaceutically active agent at a pH greater than 5.5 include, but are not limited to, organic acids. Such organic acids maintain an acidic microenvironment in the tablet, and include, but are not limited to, citric acid, fumaric acid, tartaric acid, adipic acid, glucono delta-lactone, and malic acid.

The composition of the present invention may further include other materials such as bulking agents, disintegrating agents, anti-adherants and glidants, lubricants, and binding agents.

Bulking agents include, but are not limited to, microcrystalline cellulose (eg., Avicel®, FMC Corp., Emcocel®, Mendell Inc.), mannitol, xylitol, dicalcium phosphate (eg. Emcompress, Mendell Inc.) calcium sulfate (eg. Compactrol, Mendell Inc.) starches, lactose, sucrose (Dipac, Amstar, and Nutab, Ingredient Technology), dextrose (Emdex, Mendell, Inc.), sorbitol, cellulose powder (Elcema, Degussa, and Solka Floc, Mendell, Inc.) The bulking agent may be present in the composition in an amount of from about 5 wt. % to about 90 wt. %, preferably from about 10 wt. % to about 50 wt. %.

Disintegrating agents which may be included in the composition include, but are not limited to, microcrystalline cellulose, starches, crospovidone (eg. Polyplasdone XL, International Specialty Products.), sodium starch glycolate (Explotab, Mendell Inc.), and crosscarmellose sodium (eg., Ac-Di-Sol, FMC Corp.). The disintegrating agent may be present in the composition in an amount of from about 0.5 wt. % to about 30 wt %, preferably from about 1 wt. % to about 15 wt. %.

Antiadherants and glidants which may be employed in the composition include, but are not limited to, talc, corn starch, silicon dioxide, sodium lauryl sulfate, and metallic stearates. The antiadherant or glidant may be present in the composition in an amount of from about 0.2 wt. % to about 15 wt. %, preferably from about 0.5 wt. % to about 5 wt. %.

Lubricants which may be employed in the composition include, but are not limited to, magnesium stearate, calcium stearate, sodium stearate, stearic acid, sodium stearyl fumarate, hydrogenated cotton seed oil (sterotex), talc, and waxes, including but not limited to, beeswax, carnuba wax, cetyl alcohol, glyceryl stearate, glyceryl palmitate, glyceryl behenate, hydrogenated vegetable oils, and stearyl alcohol. The lubricant may be present in an amount of from about 0.2 wt. % to about 20 wt. %, preferably from about 0.5 wt. % to about 5 wt. %.

Binding agents which may be employed include, but are not limited to, polyvinyl pyrrollidone, starch, methylcellulose, hydroxypropyl methylcellulose, carboxymethyl cellulose, sucrose solution, dextrose solution, acacia, tragacanth and locust bean gum. The binding agent may be present in the composition in an amount of from about 0.2 wt. % to about 10 wt. %, preferably from about 0.5 wt. % to about 5 wt. %.

The compositions of the present invention may be made by a direct compression method, or by a wet granulation method. In the direct compression method, the at least one pharmaceutically active agent and other ingredients are sieved through a stainless steel screen, such as a 40 mesh steel screen. The sieved materials then are charged to a suitable blender, and blended for 10 minutes with an intensifier bar on for 3 minutes. The blend then is compressed into tablets on a rotary press using appropriate tooling. The compressed tablets may be coated, if desired.

able lubricant and glidant, and the lubricated granules are compressed into tablets on a rotary press using appropriate tooling. If desired, a coating can be applied onto the compressed tablets.

The invention now will be described with respect to the following examples; however, the scope of the present invention is not intended to be limited thereby.

EXAMPLE 1

Formulations in accordance with the present invention, as well as control formulations, were prepared according to the direct compression described hereinabove. In accordance with such method, guanfacine HCl and other ingredients were sieved through a 40 mesh steel screen. The sieved materials then were charged into a Blendmaster blender (Patterson-Kelley Co.), and blended for 10 minutes with an intensifier bar on for 3 minutes. The blends then are compressed into tablets on a rotary tablet press (Stokes-Merrill Corp., Model 512) using appropriate tooling The formulations are given in Table 1 below

TABLE 1

| Ingredient | PD0052-22A 1* | PD0052-22A 2** | PD0052-25B 1 | PD0052-25B 2 | PD0052-28B 1 | PD0052-28B 2 | PD0052-32B 1 | PD0052-32B 2 | PD0052-32D 1 | PD0052-32D 2 | PD0052-39A 1 | PD0052-39A 2 |
|---|---|---|---|---|---|---|---|---|---|---|---|---|
| Guanfacine HCl | 0.57 | 1.14 | 0.57 | 1.14 | 0.57 | 1.14 | 0.57 | 1.14 | 0.57 | 1.14 | 0.57 | 1.14 |
| Lactose | 37.43 | 74.86 | — | — | — | — | 45.00 | 90.00 | 65.00 | 130.0 | — | — |
| ProSolv | 20.00 | 40.00 | — | — | 30.00 | 60.00 | — | — | — | — | 29.82 | 59.64 |
| Polyox WSR | 40.00 | 80.00 | 40.00 | 80.00 | — | — | 40.00 | 80.00 | 10.00 | 20.00 | — | — |
| Ethocel FP | — | — | — | — | 40.00 | 80.00 | — | — | — | — | 39.82 | 79.64 |
| Cellulose acetate | — | — | 50.00 | 100.00 | — | — | — | — | — | — | — | — |
| Sodium alginate | — | — | — | — | 20.00 | 40.00 | — | — | — | — | — | — |
| Carrageenan | — | — | — | — | — | — | — | — | — | — | 19.91 | 39.82 |
| Carbopol 974P | — | — | — | — | — | — | — | — | 10.00 | 20.00 | — | — |
| Fumaric acid | — | — | — | — | — | — | 5.00 | 10.00 | — | — | — | — |
| Eudragit L100-55 | — | — | — | — | — | — | — | — | 5.00 | 10.00 | — | — |
| EDTA | — | — | — | — | — | — | — | — | — | — | 0.50 | 1.00 |
| Compritol | — | — | 9.43 | 18.86 | 9.43 | 18.63 | 9.43 | 18.63 | 9.43 | 18.63 | 9.37 | 18.74 |
| Stearic acid | 2.00 | 4.00 | — | — | — | — | — | — | — | — | — | — |

*1 = composition in % weight
**2 = composition in mg per tablet
Note:
PD0052-22A and PD0052-25B contain no ionic materials in the formulations. These two formulations serve as a control.
Proslov is a trade name for silicified microcrystalline cellulose and marketed by Penwest Corp.
Polyox is a trade name for poly(ethyleneoxide) and marketed by Union Carbide.
Carbopol is a trade name for copolymer of acrylic acid and marketed by BF Goodrich.
Ethocel FP is a trade name for ethyl cellulose fine powder grade and marketed by Dow Chemical.
Eudragit L100-55 is a trade name for poly(methacrylic acid, ethyl acrylate) and marketed by Rohm GmbH.
Compritol is a trade name for glycerol behenate and marketed by Gattefosse.

In the wet granulation method, the at least one pharmaceutically active agent and other ingredients are granulated with a granulating fluid (e.g., isopropyl alcohol, ethyl alcohol, and water) in a planetary mixer, high shear mixer, or fluidized bed granulator. Binding agents may be contained in the granulating fluid, or may be in the dry mix. The wet granules are dried in an oven or fluidized bed dryer, and then sieved through a suitable screen to obtain free flowing granules. The resulting granules were blended with a suit- The dissolution data was determined as follows:

A Vankel dissolution tester (VanKel Industries, Edison, N.J.) was used for all dissolution studies. The apparatus was calibrated according to USP23. The dissolution in 0.1N hydrochloric acid (pH 1.2) or pH 6.8 phosphate buffer was tested using the paddle method (USP Apparatus II), employing 500 ml of dissolution medium at a temperature of 37° C. and an agitation rate of 50 rpm. Samples at specific time points were removed and filtered through a 35 μm filter. The filtered samples were kept in screw cap glass test tubes until analysis. An HPLC system comprised of an autosampler and a pump and a UV detector was used for sample analysis. 50 μl of the dissolution samples were injected directly on the HPLC C18 column using a mixture of acetonitrile and acetate buffer (20:80) as the mobile phase.

The dissolution data are given in Table 2 below.

TABLE 2

Dissolution Data for Guanfacine Sustained Release Tablets

| Time (hour) | PD0052-22A 1* | PD0052-22A 2** | PD0052-25B 1 | PD0052-25B 2 | PD0052-28B 1 | PD0052-28B 2 | PD0052-32B 1 | PD0052-32B 2 | PD0052-32D 1 | PD0052-32D 2 | PD0052-39A 1 | PD0052-39A 2 |
|---|---|---|---|---|---|---|---|---|---|---|---|---|
| 0.5 | 14.0 ± 0.6 | 7.0 ± 1.2 | 13.0 ± 1.5 | 5.0 ± 0.6 | 8.4 ± 2.1 | 10.0 ± 0.6 | 19.0 ± 1.2 | 12.0 ± 0.0 | 31.0 ± 1.2 | 11.0 ± 1.0 | 14.0 ± 0.6 | 10.0 ± 1.0 |
| 1.0 | 24.0 ± 1.0 | 12.0 ± 1.0 | 27.0 ± 2.0 | 7.0 ± 1.0 | 41.0 ± 1.7 | 20.0 ± 1.0 | 31.0 ± 2.6 | 20.0 ± 0.6 | 48.0 ± 1.2 | 19.0 ± 0.6 | 25.0 ± 1.0 | 18.0 ± 2.0 |
| 2.0 | 44.0 ± 0.6 | 19.0 ± 1.5 | 48.0 ± 2.5 | 11.0 ± 0.6 | 64.0 ± 2.5 | 36.0 ± 2.5 | 50.0 ± 4.2 | 35.0 ± 0.6 | 80.0 ± 5.6 | 31.0 ± 1.2 | 42.0 ± 1.0 | 31.0 ± 4.0 |
| 3.0 | 59.0 ± 0.6 | 26.0 ± 1.5 | 63.0 ± 1.7 | 14.0 ± 0.6 | 77.0 ± 2.6 | 49.0 ± 3.6 | 65.0 ± 6.1 | 49.0 ± 1.0 | 96.0 ± 5.0 | 46.0 ± 0.6 | 56.0 ± 2.6 | 46.0 ± 4.4 |
| 4.0 | 71.0 ± 6.0 | 31.0 ± 2.9 | 74.0 ± 1.5 | 16.0 ± 0.6 | 86.0 ± 3.2 | 59.0 ± 3.2 | 77.0 ± 5.5 | 61.0 ± 1.0 | 104 ± 3.5 | 56.0 ± 0.6 | 69.0 ± 3.0 | 56.0 ± 5.8 |
| 6.0 | 90.0 ± 2.0 | 39.0 ± 2.5 | 86.0 ± 1.7 | 19.0 ± 0.0 | 97.0 ± 3.5 | 71.0 ± 5.0 | 99.0 ± 4.4 | 87.0 ± 2.5 | 111 ± 4.0 | 74.0 ± 1.2 | 90.0 ± 2.6 | 72.0 ± 6.2 |
| 8.0 | 99.0 ± 1.7 | 46.0 ± 2.5 | 93.0 ± 2.1 | 21.0 ± 1.0 | 108 ± 3.8 | 80.0 ± 5.5 | 102 ± 1.2 | 97.0 ± 1.5 | 112 ± 4.0 | 89.0 ± 2.3 | 102 ± 2.3 | 83.0 ± 6.4 |
| 12.00 | 105.0 ± 1.5 | 61.0 ± 4.7 | 100.0 ± 1.2 | 25.0 ± 1.0 | 113 ± 3.6 | 91.0 ± 6.0 | 103 ± 2.3 | 98.0 ± 1.0 | 113 ± 3.8 | 107 ± 2.9 | 112 ± 0.6 | 96.0 ± 4.2 |

*1 = percent dissolved using a pH 1.2 dissolution medium
**2 = percent dissolved using a pH 6.8 dissolution medium
Note:
The data represent the mean percent dissolved ± standard deviation of three replicates.

The above results show that the compositions of the present invention have improved dissolution profiles when compared with the control compositions.

EXAMPLE 2

The solubility of anagrelide HCl in aqueous solutions in the pH range of 1 to 11.4 at 25° C. was determined. The solubility-pH profile of anagrelide HC1 is shown in FIG. 1. Below pH 3, the solubility increased as the pH decreased which is consistent with formation of a more soluble protonated form. At pH 0.96 the solubility was 236 mcg/mL. Above pH 4, the solubility was independent of pH and remained constant (ca. 1.2 mcg/mL) up to pH 8. Above pH 8, the solubility increased with increasing pH which is due to the ionization of the quinazoline moiety. The solubility at pH 11.4 was 992 mcg/mL.

Formulations I through IV were formulated according to the procedure described in Example 1, except that anagrelide HCl has been substituted for guanfacine HCl.

The formulations are given in Table 3 below.

TABLE 3

| Ingredients | Formulation I mg/Tablet | Formulation I % | Formulation II mg/Tablet | Formulation II % | Formulation III mg/Tablet | Formulation III % | Formulation IV mg/Tablet | Formulation IV % |
|---|---|---|---|---|---|---|---|---|
| Anagrelide HCl | 2.44 (2.0 base) | 1.22 | 2.44 (2.0 base) | 1.22 | 2.44 (2.0 base) | 1.22 | 2.44 (2.0 base) | 1.22 |
| Polyox WSR 301 | 30.00 | 15.00 | 50.00 | 25.00 | | | | |
| Prosolv HD 90 | 60.00 | 30.00 | 60.00 | 30.00 | 66.00 | 33.00 | 80.00 | 40.00 |
| Fujicalin SG * | 60.00 | 30.00 | 30.00 | 15.00 | 60.00 | 30.00 | 40.00 | 20.00 |
| Eudragit L 100-55 | 20.00 | 10.00 | 30.00 | 15.00 | 24.00 | 12.00 | 20.00 | 10.00 |
| Ethocel Std. 100 FP | | | | | 30.00 | 15.00 | | |
| Fumaric Acid | 10.00 | 5.00 | 10.00 | 5.00 | | | | |
| Compritol 888 ATO | 17.56 | 8.78 | 17.56 | 8.78 | 17.56 | 8.78 | 17.56 | 8.78 |
| Polyox WSR N80 | | | | | | | 40.00 | 20.00 |
| Formulation # | PD0073-55A | | PD0073-57A | | PD0073-64A | | PD0073-78A | |
| Total | 200.00 | 100.00 | 200.00 | 100.00 | 200.00 | 100.00 | 200.00 | 100.00 |

* Fujicalin SG is a dibasic calcium phosphate sold by Fuji Chemical Co., Ltd.

A Vankel dissolution tester (VanKel Industries, Edison, N.J.) was used for all dissolution studies. The apparatus was calibrated according to USP 23. The dissolution in 0.1N hydrochloric acid (pH 1.1) with 0.1% Tween 80 or pH 6.8 phosphate buffer with 0.1% Tween 80 was tested using the paddle method (USP Apparatus II), employing 900 ml of dissolution medium at a temperature of 37° C., and an agitation rate of 100 rpm. Samples at specific time points were removed and filtered through a 70 μm filter. The filtered samples were kept in screw cap glass test tubes until analysis. An HPLC system composed of an autosampler and a pump and a UV detector was used for sample analysis. 20 μl of the dissolution samples were injected directly on the HPLC C18 column using a mixture of acetonitrile and ammonium acetate buffer (36:64) as the mobile phase.

The dissolution data are given in Table 4 below.

TABLE 4

Dissolution Data for Anagrelide Sustained Release Tablets

| Time (hour) | PD0073-55A | | PD0073-57A | | PD0073-64A | | PD0073-78A | |
|---|---|---|---|---|---|---|---|---|
| | 1* | 2** | 1 | 2 | 1 | 2 | 1 | 2 |
| 0.5 | N/A | 4.0 ± 0.6 | 6.0 ± 0.0 | 2.0 ± 0.0 | 27.0 ± 2.1 | 5.0 ± 1.0 | 16.0 ± 0.6 | 12.0 ± 1.2 |
| 1.0 | 13.0 ± 0.6 | 6.0 ± 0.0 | 9.0 ± 0.6 | 3.0 ± 0.0 | 39.0 ± 3.1 | 11.0 ± 2.9 | 27.0 ± 1.5 | 30.0 ± 1.0 |
| 2.0 | 21.0 ± 0.6 | 10.0 ± 0.6 | 15.0 ± 0.6 | 7.0 ± 0.0 | 52.0 ± 4.5 | 31.0 ± 3.2 | 43.0 ± 3.6 | 56.0 ± 1.7 |
| 4.0 | 40.0 ± 2.5 | 22.0 ± 1.2 | 30.0 ± 2.3 | 16.0 ± 0.6 | 69.0 ± 5.3 | 58.0 ± 3.5 | 55.0 ± 4.4 | 72.0 ± 1.2 |
| 8.0 | 72.0 ± 5.0 | 57.0 ± 7.4 | 57.0 ± 2.0 | 39.0 ± 1.0 | 85.0 ± 2.6 | 73.0 ± 2.6 | 67 ± 5.5 | 78.0 ± 0.6 |
| 12.0 | 95.0 ± 2.9 | 77.0 ± 5.3 | 77.0 ± 2.1 | 62.0 ± 3.6 | 88.0 ± 1.0 | 79.0 ± 2.1 | 83 ± 3.6 | 82.0 ± 0.0 |

*1 = percent dissolved using a pH 1.1 dissolution medium with 0.1% Tween 80.
**2 = percent dissolved using a pH 6.8 dissolution medium with 0.1% Tween 80.
Note:
The data represent the mean percent dissolved ± standard deviation of three replicates.

It is to be understood, however, that the scope of the present invention is not to be limited to the specific embodiments described above. The invention may be practiced other than as particularly described and still be within the scope of the accompanying claims.

What is claimed is:

1. A pharmaceutical composition, comprising:
   (a) at least one pharmaceutically active agent that is pH dependent:
   (b) at least one non-pH dependent sustained release agent; and
   (c) at least one pH dependent agent that increases the rate of release of said at least one pharmaceutically active agent from the tablet at a pH in excess of 5.5.

2. The composition of claim 1 wherein said at least one pH dependent agent is at least one polymer that swells at a pH in excess of 5.5.

3. The composition of claim 1 wherein said at least one pH dependent agent is at least one enteric agent.

4. The composition of claim 1 wherein said at least one pH dependent agent is at least one agent that increases the solubility of said at least one pharmaceutically active agent at a pH of greater than 5.5.

5. The composition of claim 1 wherein said at least one pharmaceutically active agent is selected from the group consisting of guanfacine hydrochloride, anagrelide, guanethidine monosulfate, quanadrel sulfate, resirpine, propanolol, metoprolol, atenolol, timolol, erythromycin, clonidine, chlorpheniramine, bromopheniramine, diltiazem, and scopolamine.

6. The composition of claim 5 wherein said at least one pharmaceutically active agent guanfacine hydrochloride.

7. The composition of claim 5 wherein said at least one pharmaceutically active agent is anagrelide hydrochloride.

8. The composition of claim 1 wherein said non-pH dependent sustained release agent is selected from the group consisting of ethylcellulose, cellulose acetate, vinyl acetate/vinyl chloride copolymers, acrylate/methacrylate copolymers, polyethylene oxide, hydroxypropyl methylcellulose, carageenan, alginic acid and salts thereof, hydroxyethyl cellulose, hydroxypropyl cellulose, karaya gum, acacia gum, trgacanth gum, locust bean gum, guar gum, sodium carboxymethyl cellulose, methyl cellulose, beeswax, carnauba wax, cetyl alcohol, hydrogenated vegetable oils, and stearyl alcohol.

9. The composition of claim 2 wherein said at least one polymer that swells at a pH in excess of 5.5 is selected from the group consisting of acrylic acid copolomers, sodium alginate, carrageenan, alginic acid, pectin, and sodium carboxymethyl cellulose.

10. The composition of claim 3 wherein said at least one enteric agent is selected from the group consisting of cellulose acetate phthalate, hydroxypropyl methylcellulose phthalate, polvinyl acetate phthalate, methacrylic acid copolymers, cellulose acetate trimellitate, hydroxypropyl methylcellulose acetate, succinate, shellac, and zein.

11. The composition of claim 4 wherein said at least one agent that increase the solubility of said at least one pharmaceutically active agent at a pH greater than 5.5 is at least one organic acid.

12. The composition of claim 11 wherein said at least one organic acid is selected from the group consisting of citric acid, fumaric acid, tartaric acid, adipic acid, glucono delta-lactone, and malic acid.

13. The composition of claim wherein said pH-dependent agent that increase the rate of release of the at least one pharmaceutically active agent from the tablet at a pH in excess of 5.5 is an agent that maintains an acidic microenvironment in the composition.

14. The composition of claim 12 wherein said organic acid is fumaric acid.

15. The composition of claim 1 and further comprising a binding agent.

16. The composition of claim 15 wherein said binding agent is selected from the group consisting of polyvinyl pyrrolidone, starch, methylcelluose, hydroxypropyl methylcelluose, carboxymethyl cellulose, sucrose solution, dextrose solution, acacia, tragacanth, and locust bean gum.

17. The composition of claim 16 wherein said binder is hydroxypropyl methylcellulose.

18. The composition of claim 1 wherein said pharmaceutically active agent is present in the composition in an amount of from about 0.1 wt. % to about 70 wt .%.

19. The composition of claim 18 wherein said pharmaceutically active agent is present in the composition in an amount of from about 1 wt. % to about 40 wt. %.

20. The composition of claim 1 wherein said non-pH-dependent sustained release agent is present in the composition in an amount of from about 5 wt. % to about 50 wt. %.

21. The composition of claim 20 wherein said non-pH-dependent sustained release agent is present in the composition in an amount of from about 10 wt. % to about 30 wt. %.

22. The composition of claim 1 wherein said at least one pH-dependent agent is present in the composition in an amount of from about 0.5 wt. % to about 40 wt. %.

23. The composition of claim 22 wherein said at least one pH-dependent agent is present in the composition in an amount of from about 1 wt. % to about 20 wt. %.

24. The composition of claim 8 wherein said non-pH-dependent sustained release agent is ethylcellulose.

25. The composition of claim 8 wherein said non-pH-dependent sustained release agent is hydroxypropyl methylcellulose.

26. The composition of claim 8 wherein said non-pH-dependent sustained release agent is an acrylate/methacrylate copolymer.

27. The composition of claim 8 wherein said non-pH-dependent sustained release agent is polyethylene oxide.

28. The composition of claim 9 wherein said at least one polymer that swells at a pH in excess of 5.5 is sodium alginate.

29. The composition of claim 10 wherein said at least one enteric agent is a methacrylic acid copolymer.

30. The composition of claim 1 wherein said composition is in the form of a tablet.

* * * * *